(12) United States Patent
Hughes

(10) Patent No.: US 9,358,114 B2
(45) Date of Patent: Jun. 7, 2016

(54) INTRAOPERATIVE SCANNING FOR IMPLANT OPTIMIZATION

(75) Inventor: Michael Dean Hughes, Cordova, TN (US)

(73) Assignee: Smith & Nephew, Inc., Memphis, TN (US)

( * ) Notice: Subject to any disclaimer, the term of this patent is extended or adjusted under 35 U.S.C. 154(b) by 596 days.

(21) Appl. No.: 13/817,158

(22) PCT Filed: Aug. 25, 2011

(86) PCT No.: PCT/US2011/049153
§ 371 (c)(1),
(2), (4) Date: Feb. 15, 2013

(87) PCT Pub. No.: WO2012/027574
PCT Pub. Date: Mar. 1, 2012

(65) Prior Publication Data
US 2013/0144392 A1    Jun. 6, 2013

Related U.S. Application Data

(60) Provisional application No. 61/376,853, filed on Aug. 25, 2010, provisional application No. 61/480,761, filed on Apr. 29, 2011.

(51) Int. Cl.
| | |
|---|---|
| *A61F 2/30* | (2006.01) |
| *A61B 17/15* | (2006.01) |
| *A61B 19/00* | (2006.01) |
| A61B 17/56 | (2006.01) |
| A61F 2/38 | (2006.01) |
| A61F 2/46 | (2006.01) |

(52) U.S. Cl.
CPC ............ *A61F 2/30* (2013.01); *A61B 17/157* (2013.01); *A61B 19/50* (2013.01); *A61B 2017/564* (2013.01); *A61B 2017/568* (2013.01); *A61B 2019/504* (2013.01); *A61B 2019/508* (2013.01); *A61F 2/38* (2013.01); *A61F 2002/4633* (2013.01)

(58) Field of Classification Search
CPC ............... A61B 5/004; A61B 5/0062; A61B 2019/5231; A61B 19/3437
See application file for complete search history.

(56) References Cited

U.S. PATENT DOCUMENTS

| | | | |
|---|---|---|---|
| 2004/0133276 A1* | 7/2004 | Lang | A61F 2/30756 623/14.12 |
| 2005/0149041 A1* | 7/2005 | McGinley | A61B 17/155 606/88 |

(Continued)

OTHER PUBLICATIONS

Australian Patent Office, Patent Examination Report No. 1, Aug. 26, 2013, 3 pages.

(Continued)

*Primary Examiner* — Yashita Sharma
*Assistant Examiner* — Daniel Bissing
(74) *Attorney, Agent, or Firm* — David A. Chambers

(57) ABSTRACT

Systems and methods for implant optimization using intraoperative scanning are set forth. According to one embodiment, a method comprising intraoperatively scanning a joint surface, processing the scan and creating a three-dimensional computer model, performing simulations with the three-dimensional computer model, determining an optimal implant attribute from analysis of the simulations, selecting an optimal implant, determining an ideal positioning and orientation of the selected implant relative to scanned anatomical features, rapidly creating a patient-matched guide to facilitate bone surface preparation in order to achieve ideal positioning and orientation of the selected implant, preparing the surface using the patient matched guide, and implanting the optimal implant is set forth.

17 Claims, 6 Drawing Sheets

(56) References Cited

U.S. PATENT DOCUMENTS

| | | | | |
|---|---|---|---|---|
| 2007/0185498 A2* | 8/2007 | Lavallee | ............... | A61B 17/154 606/102 |
| 2011/0196377 A1* | 8/2011 | Hodorek | ............... | A61B 17/155 606/87 |
| 2013/0292870 A1* | 11/2013 | Roger | ................... | A61B 17/155 264/138 |

OTHER PUBLICATIONS

China Patent Office, First Office Action, dated Jul. 22, 2014, 3 pages with translation.

Chinese Patent Office, Second Office Action, dated May 20, 2015, 8 pages including English translation.

Mexico Patent Office, First Office Action, dated Oct. 7, 2015, 6 pages including English translation.

* cited by examiner

INTRAOPERATIVE SCANNING FOR IMPLANT OPTIMIZATION

RELATED APPLICATIONS

This application is a U.S. National Phase filing of International Application No. PCT/US11/049153 filed on Aug. 25, 2011 which claims priority to U.S. provisional patent application 61/376,853 filed on Aug. 25, 2010 and U.S. provisional patent application 61/480,761 filed on Apr. 29, 2011, each of which are incorporated in their entirety by this reference.

RELATED FIELDS

Systems, methods, instruments and other components for knee and other joint arthroplasty procedures.

BACKGROUND

Joint arthroplasty, such as the replacement of one or more articular surfaces of a knee joint with an artificial implant, is a complex procedure. Such procedures often require modifications of the patient's anatomy to prepare it to receive the implant. In some instances, such modifications involve resecting, milling or otherwise removing existing bone, cartilage and/or other tissue from the patient's anatomy. The positions and orientations of these modifications can determine position and orientation of the artificial implant relative to the patient's anatomy once installed in at least some degrees of freedom. Obtaining a proper position and orientation of the implant can be an important factor in the success of the joint arthroplasty procedure, and, as such, it will be important, in at least some instances, to properly position and/or orient the resections and/or other modifications to the anatomy.

Conventionally, standardized cutting blocks and other generic instrumentation sets have been used to guide modifications to the anatomy in a joint arthroplasty. In some instances, the cutting blocks and other instrumentation has been specifically designed for use with a particular patient. Existing instrumentation, methods and systems have drawbacks, however, and the present invention provides embodiments that improve on at least some of those drawbacks.

SUMMARY

Embodiments of the present invention provide systems and methods that use intraoperative imaging data to customize cutting blocks, other instrumentation, or other surgical aids in order to enhance the accuracy of bone, articular cartilage and/or other anatomy preparation and implant placement. In one embodiment, such a method may include one or more steps of intraoperatively scanning a joint surface, processing the scan, creating a three-dimensional computer model, performing simulations with the three-dimensional computer model, determining an optimal implant attribute from analysis of the simulations, selecting an optimal implant, determining an ideal positioning and orientation of the selected implant relative to scanned anatomical features, rapidly creating a patient-matched guide to facilitate modifications to the bone and other anatomy in a manner that achieves ideal positioning and orientation of the selected implant in at least some degrees of freedom, modifying the anatomy using the patient matched guide, and/or implanting the optimal implant.

Embodiments of the present invention include a surgical system comprising a scanner capable of intraoperatively scanning a body part to obtain scan data, an image processor capable of communicating with the scanner and configured to create a body part model, a modeling processor capable of communicating with the image processor and configured to simulate interaction of the body part model with at least one other component and further configured to determine at least one optimal implant attribute based at least in part on the simulated interaction, an implant component having at least one feature determined based at least in part on a first of the at least one optimal implant attribute, and a preparation guide configured based at least in part on a second of the at least one optimal implant attribute. The first and second optimal attributes may be the same. According to other embodiments, a method of intraoperatively scanning at least a portion of a knee joint to obtain intraoperative scan data, rendering a three dimensional model of the knee joint based at least in part on the intraoperative scan data, simulating interaction of the body part model with at least one other component and further determining at least one optimal implant attribute based at least in part on the simulated interaction, selecting an implant component having at least one feature determined based at least in part on the optimal implant attribute, and providing a preparation guide configured based at least in part on the optimal implant attribute is provided.

According to certain embodiments, the surgical system or method can be configured for use in a total knee arthroplasty procedure. In certain embodiments, the body part comprises one or more of a distal end of a femur, proximal end of a tibia, proximal end of a fibula, a patella, knee joint or ligament attachment point. In still other embodiments, the image processor creates a three dimensional body part model, which can be a knee joint. In yet other embodiments, the modeling processor is configured to simulate interaction of the body part model with one or more of an implant component, another body part, or a preparation guide. In other embodiments, an optimal implant attribute identifies a size of the implant component, position or orientation of an implant component, or alignment of an implant component. In certain embodiments, the size of the implant component is determined based at least in part on the optimal implant attribute.

According to still other embodiments, the preparation guide can be a patient matched preparation guide, a cutting block, adjustable preparation guide, can be selected from a set of guides based on the optimal implant attribute, or can be rapid prototyped. In certain embodiments the modeling processing can allow a user to experiment with variety of simulated implant configurations and can be configured to identify which implant configuration best achieves a desired performance metric In other embodiments, the modeling processor can be configured to combine the scan data with image data from pre-operative scanning.

In certain embodiments, image data can be obtained preoperatively to identify a mechanical axis. In other embodiments, the body part model includes kinematics or biomechanics information and can represent a model of a joint and comprise articular surface attributes. Such articular surface attributes can include one or more of tibial rotation, femoral rollback, patellar alignment, or quadriceps efficiency. According to certain embodiments the modeling processing is configured to determine performance metrics such as a desired patellafemoral joint line.

According to other embodiments, A CAS system capable of monitoring actual surgical results is utilized and the modeling processor is further configured to compare predicted surgical results with the actual surgical results. In still other embodiments, the modeling processor is capable of receiving second intraoperative scan data and is configured to compare actual placement of an implant component with a predicted placement based on the second intraoperative scan data. The modeling processor and image processor can comprise a single physical central processing unit or can comprise separate physical processing units.

According to certain embodiments, a method for implanting an implant relative to a joint, including exposing through one or more incisions a joint of a patient, scanning the exposed joint using an optical scanner to obtain image data, using the image data, creating a computer model of the joint, using the computer model of the joint and a computer processor, identifying at least one optimal implant attribute, and implanting an implant relative to the joint including the identified optimal implant attribute is provided. According to certain embodiments, the exposed joint is a knee joint and the method may comprise exposing an articular surfaces and ligament attachment points associated with the knee joint. According to other embodiments, a topographical scanner is used to scan the joint. According to yet other embodiments, the method can further include marking ligament attachment points associated with the joint prior to scanning the exposed joint.

In other embodiments, scanning the exposed joint can comprise scanning surfaces associated with a tibia, a femur, and a patella. In certain embodiments, creating the computer model of the joint comprises creating a three-dimensional computer model of the joint, and may optionally include incorporating information relating a mechanical axis to the joint. In yet other embodiments, creating the computer model of the joint comprises incorporating information relating at least one ligament attachment location to the joint. In certain embodiments, identifying at least one optimal implant attribute can comprise using the computer processor and the computer model of the joint to simulate the implant implanted relative to the joint. Moreover, in other embodiments, simulating the implant implanted relative to the joint may comprise simulating movement of the joint after implantation of the implant; simulating a potential implant component for implantation relative to the joint; simulating a possible implant component selected from a library of possible implant components; or simulating a potential implant position and orientation for implantation relative to the joint.

According to other embodiments, the method may further include using the computer model of the joint and the identified optimal implant attribute to determine custom bone preparation information. In certain embodiments, the custom bone preparation information can be used to rapidly manufacture a custom cutting guide. In other embodiments, the custom bone preparation information may be used to adjust an adjustable cutting device. In other embodiments, the method may further include implanting an implant relative to the joint including the identified optimal implant attribute.

According to other embodiments, methods for exposing through one or more incisions a knee joint of a patient, including articular surfaces and ligament attachment points associated with the knee joint, marking the ligament attachment points, scanning the exposed joint including the marked ligament attachment points using an optical scanner to obtain image data, using the image data, creating a computer model of the joint incorporating information relating to the ligament attachment points relative to the joint, using the computer model of the joint and a computer processor, identifying at least one optimal implant attribute, and implanting an implant relative to the joint including the identified optimal implant attribute are set forth. In certain embodiments, identifying the at least one optimal implant attribute comprises using the computer processor and the computer model of the joint to simulate the implant implanted relative to the joint.

In still another embodiment, a method for implanting an implant relative to a joint, comprising exposing through one or more incisions a knee joint of a patient, scanning the exposed joint using an optical scanner to obtain image data, using the image data, creating a computer model of the joint, using the computer model of the joint and a computer processor, identifying at least one optimal implant attribute, wherein identifying the at least one optimal implant attribute comprises using the computer processor and the computer model of the joint to simulate the implant implanted relative to the joint, and implanting an implant relative to the joint including the identified optimal implant attribute is set forth.

DETAILED DESCRIPTION

Embodiments of the present invention can be understood more readily by reference to the following detailed description, examples, and drawings and their previous and following descriptions. However, apparatus, systems and methods of the present invention are not limited to the specific embodiments presented in the detailed description, examples, and drawings. It should be recognized that these embodiments are merely illustrative of the principles of the present invention. Numerous modifications and adaptations thereof will be readily apparent to those of skill in the art without departing from the spirit and scope of the invention.

Figure 1:
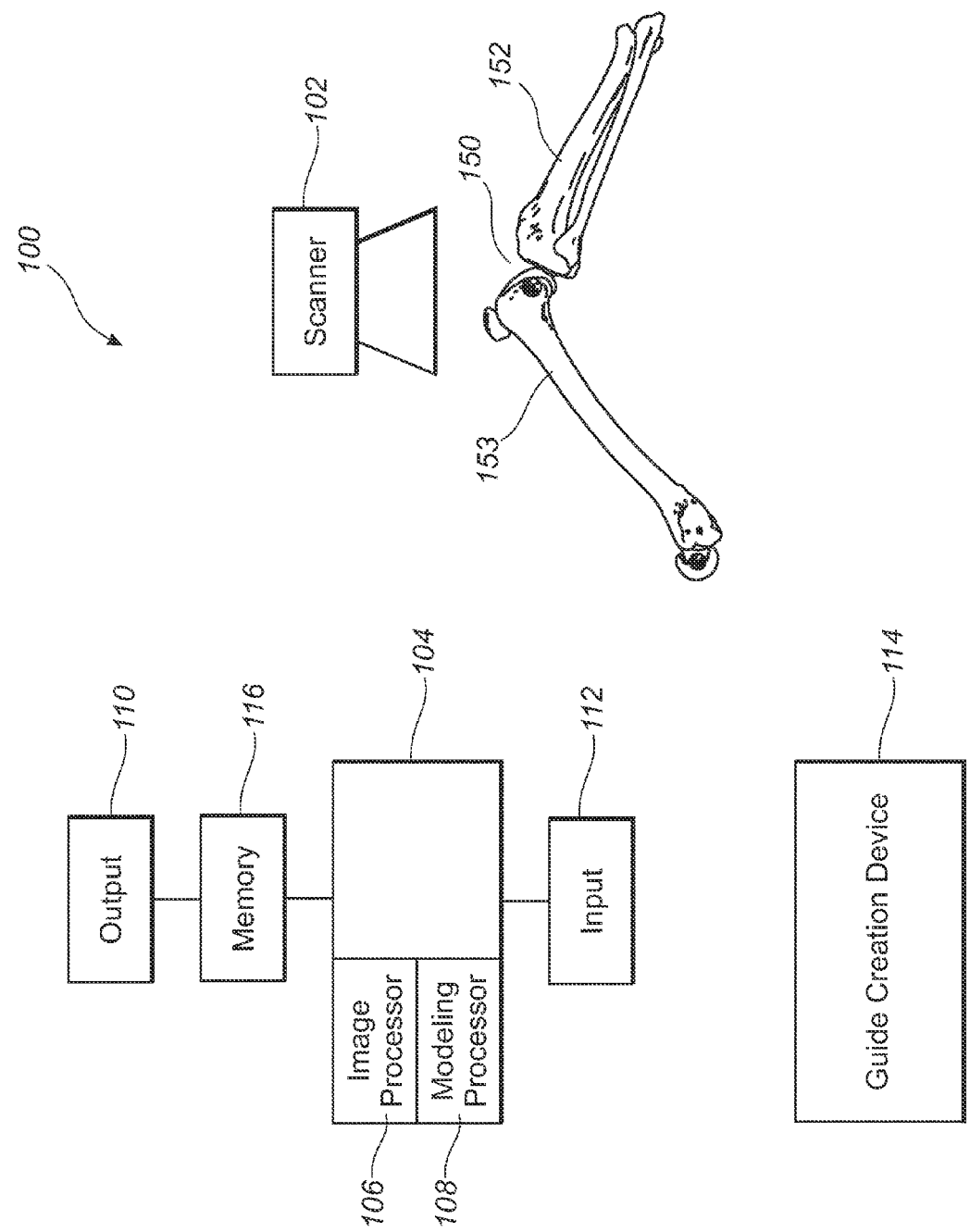
FIG. 1 illustrates a sample system for use with various embodiments of the present invention.

Referring to the figures wherein like numerals indicate like elements throughout the various figures, FIG. 1 shows a surgical environment 100 for performing a knee arthroplasty procedure. The illustrated environment 100 contains scanning equipment 102 suitable for obtaining a image of the joint 150. The scanning equipment 102 can be a handheld scanner or may be stationed on a surgical table, fixture, jig, or some portion of the operating room such as the wall or ceiling. According to certain embodiments, the scanning equipment may be a laser scanner or other suitable topographical scanner. Also shown in FIG. 1 is processing unit 104, which includes image processor 106 and modeling processor 108. Image processor 106 can receive data from the scanning equipment 102 and prepare the data for receipt by the modeling processor 108. The modeling processor 108 can then receive the data and produce a three-dimensional image of the scanned knee joint, which can be stored in memory 116 and output to output device 110. For example, output device 110 can display a three-dimensional model of the joint which the user can manipulate with input devices 112. Such manipulations may include rotating, zooming, panning, etc.

In addition to the three-dimensional model of the joint, processing unit 104 can also output (or, in some embodiments, access from a pre-existing database) a three-dimensional model of possible implant components and cause the three-dimensional model of the possible implant components to interact with the three-dimensional model of the joint in a manner indicating predicted real world performance. In this way, a surgeon can virtually experiment with various implant sizes, positions, orientations and/or other variables. For example, the surgeon can use the virtual simulation to determine an ideal bone resection in order to obtain the desired joint positioning and alignment by varying slightly the resection or resections positions and orientations and allowing the modeling processor to simulate and compare performance of the implant and joint with the various resulting implant orientations resulting from the proposed resections.

Also shown in FIG. 1 is guide creation device 114. Guide creation device 114 can include rapid manufacturing technology such as additive or subtractive manufacturing equipment. For example, selective laser sintering can be used to rapidly create a guide made from nylon or another suitable polymer, metal, or blend of polymers, metals and/or other materials. In certain embodiments, a reusable device can be used, which can comprise a number of adjustable guide components with set screws, knobs, or similar adjustable features that lock, release, adjust, and rotate modular components with respect to each other in order to achieve a desired guide configuration.

Figure 2:
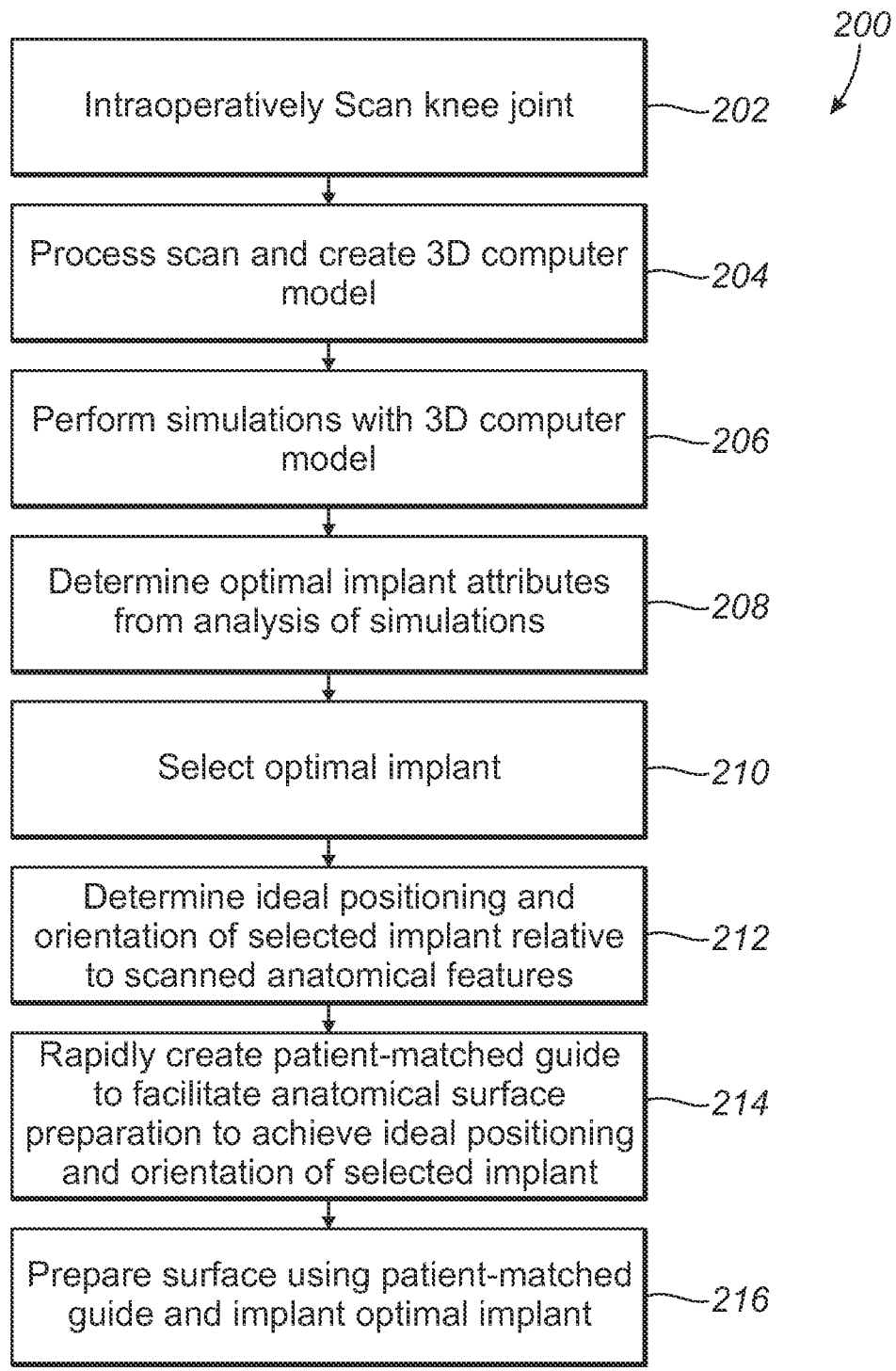
FIG. 2 illustrates a sample method that may be carried out according to various embodiments of the present invention.

FIG. 2 illustrates a method 200 that may be used according to certain embodiments of the present invention. Prior to performing the example method 200, a patient is prepared for surgery in typical fashion and the knee which is undergoing the arthroplasty is exposed through one or more incisions. Once the articular or other surfaces of the knee are exposed, or at least certain portions thereof, an optical scan 202 of the knee joint may be performed. The scan may be obtained using laser interferometry, for example, or other optical scanning technique suitable for obtaining a detailed image of the knee. The optical scan may capture image data of the knee anatomy, articulation surfaces, ligament attachment points and/or other features of the joint. The use of a topographical scanner, in at least some embodiments, may have advantages over pre-surgical MRI or CT based imaging methods in that it is not necessary to compile image "slices" as are obtained from MRI and CT scans and to then interpolate between the slices, often performed in 2 mm sections. Thus, no segmentation of the scanned anatomy is required (in at least some embodiments) and a more accurate representation of the anatomy including the articulation surfaces and ligament attachment points may be obtained in certain instances. As part of capturing image data, markers may be used to enhance the ability to capture ligament attachment points during the optical scan. Such markers may be active or passive infrared markers for use with a CMM system, can include a reflector for use with a laser-based CMM system, or may comprise other suitable devices configured to mark the ligament attachment point in the optical scan. By obtaining image data intra-operatively through the use of an optical scanner, the image data more accurately reflects the patient's anatomy at the time of surgery than would image data obtained weeks prior to surgery as may be the case with pre-operative MRI data. Additionally, intra-operative optical scanning can yield higher resolution image data as compared to MRI data, and can make ligament attachment points easier to identify even in situations where markers are not used to enhance identification of ligament attachment locations.

Once an optical scan of the knee joint is obtained, the particular embodiment of method 200 proceeds to block 204 wherein the image data is processed to create a three-dimensional computer model of the knee joint incorporating the scanned image data. Processing the raw image data may include employing smoothing functions, interpolations, or other data processing techniques in order to coordinate the image data with a computer model of the knee joint. Processing optical image data from the intra-operative scan is generally faster than processing on MRI data due to the segmentation of MRI images. The computer model of the knee joint can include information regarding the mechanical axes obtained from a pre-operative standing x-ray and coordinate that information with image data representing bone morphology and ligament attachment points as obtained from the intra-operative optical scanning.

Figure 3:
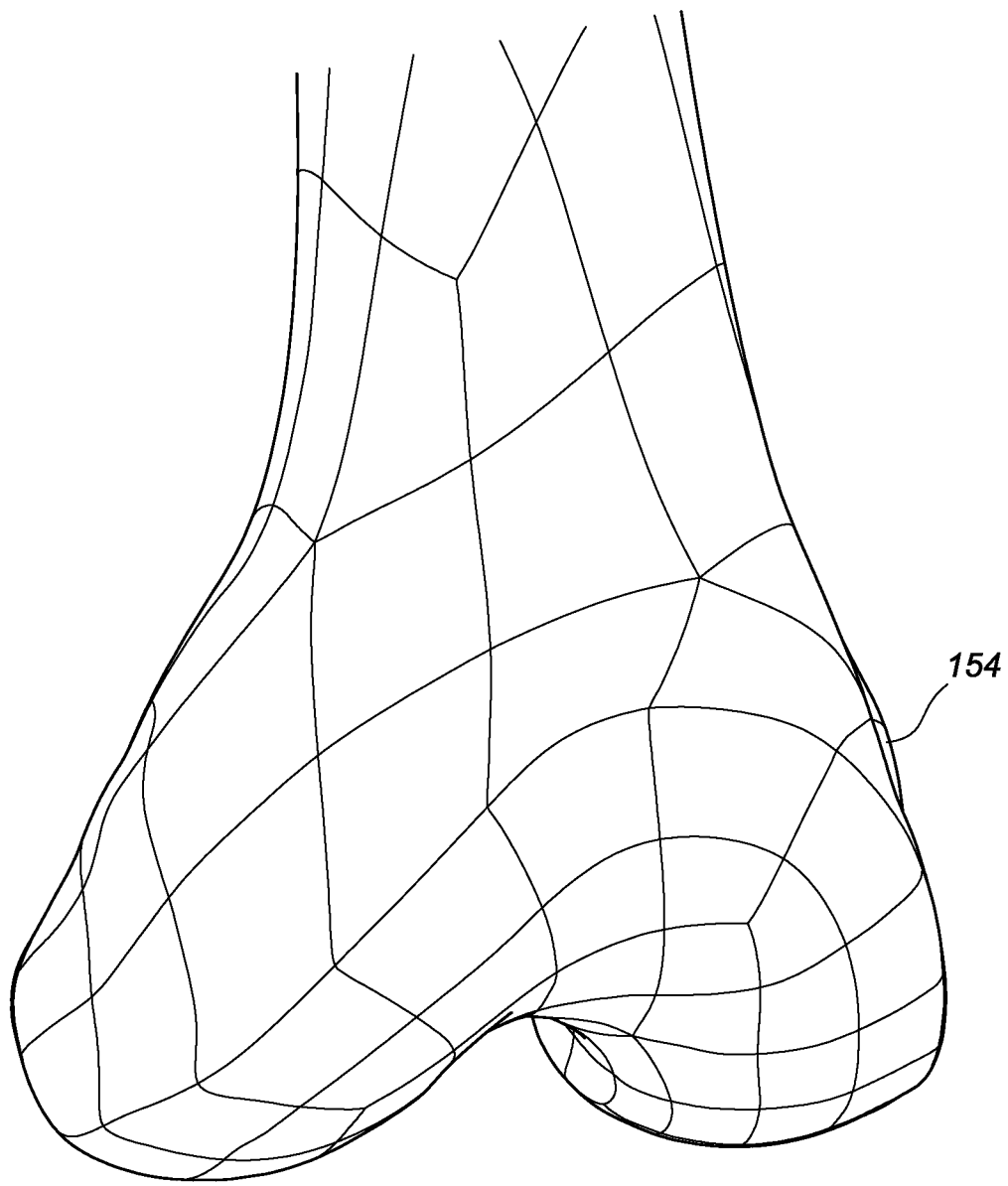
FIG. 3 illustrates a model of a bone surface, in this particular embodiment, of a distal femur.
Figure 4:
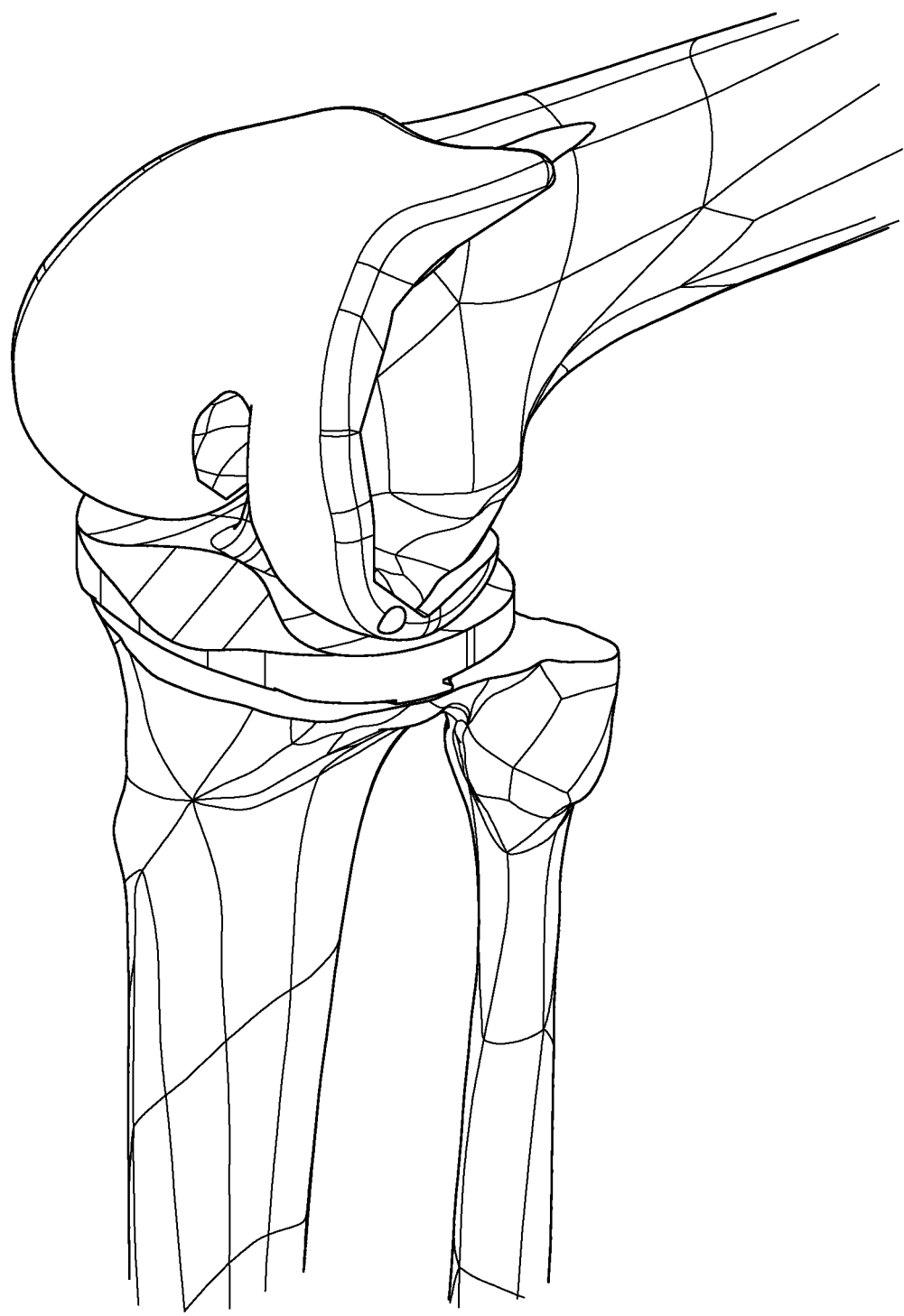
FIG. 4 illustrates a three-dimensional computer model of a joint with simulated implant components.

Once the image data is suitably processed, the computer functionality can render a three-dimensional model of the knee joint that includes information identifying the mechanical axes, morphology, and ligament attachment points. For example, the computer functionality can render the three-dimensional model by creating a mathematical model describing the surface geometry of the bones comprising the joint 150, which can be used in stereolithograpy CAD software such as an .STL file. FIG. 3 illustrates a surface model 154 of femur 153 which comprises a part of joint 150 as may be rendered by the modeling processor 108, stored in memory 116, and output via output 110. A surface model 154 of femur 153 can be combined with a computer generated surface model of tibia 152, together with surface models of implant components to create a three-dimensional model of the joint 150 as shown in FIG. 4. In the particular embodiment shown in FIG. 4, the three-dimensional model includes femoral and tibial implant components implanted on proposed resections and otherwise positioned and oriented in selected manners. In some embodiments, several models of the joint 150 can be created having different resection and/or implant positions, orientations, sizes, and/or other configurations. Although not shown in the Figures, in some embodiments, the joint model may also include or otherwise incorporate information in addition to just the three dimensional anatomy of the femur, tibia, and/or patella. For instance, in some embodiments, the joint model may also reflect information concerning ligament and other soft tissue attachment points, and/or other information concerning the kinematics, biomechanics, and/or other data about the patient's joint.

Once a three-dimensional model of the knee joint is obtained, the embodiment of method 200 proceeds to block 206 wherein simulations are preformed using the three-dimensional computer model. To create simulations using the three-dimensions model, software such as LifeMOD's KneeSim software, computer assisted surgery (CAS) software, finite element analysis (FEA) programs, or other suitable modeling software can be used. The simulation software can virtually model the movement of the knee in conjunction with various potential implant components in order to analyze attributes of the implant and articular surfaces such as proper tibial rotation, femoral rollback, patellar alignment, quadriceps efficiency and to generally enhance durability and robustness of the implants and knee joint. By using a computer generated simulation of the knee, a wide range of parameters can be experimentally viewed and hundreds of possible implementations can be tested to optimize for all possible variations.

By analyzing the simulations with the three-dimensional computer model (such as the model shown in FIG. 4), optimal implant attributes can be determined in step 208 in the particular embodiment illustrated by FIG. 2. Analysis of the simulation can be done manually or with the aid of software for identifying which implant attributes best achieve desired performance metrics. For example, software can be used to determine which size of a prosthetic component best achieves the desired petallafemoral joint line while aligning with surrounding anatomical structures.

The set of optimal implant attributes such as sizing, shape, or composition (for example) can be used in step 210 to select an optimal implant conforming to the identified attributes. The implant can be selected from a library of pre-made implants or can be created based on the identified attributes.

Once an optimal implant has been selected, an ideal positioning and orientation of the selected implant relative to the scanned anatomical features is determined in step 212. As with implant selection, proper positioning can be performed manually by an experienced surgeon or other user, or can be facilitated by the modeling processor 108. For example, the modeling processor 108 can create a simulated three-dimensional representation of the bone surfaces comprising the joint 150 and also create a simulated three-dimensional representation of the implant components as seen in FIG. 4. Modeling processor 108 can then move the simulated three-dimensional representation of the joint and implant components through a variety of positions and orientations to simulate real world movement, loads, and stresses and account for patient-specific bone morphology and ligament attachment points. Because the modeling processor 108 can simulate real world loads and stresses and also account for the patient-specific morphology and ligament attachment points, an optimal location and corresponding bone preparation can be determined in order to achieve the desired implant results.

Figure 5:
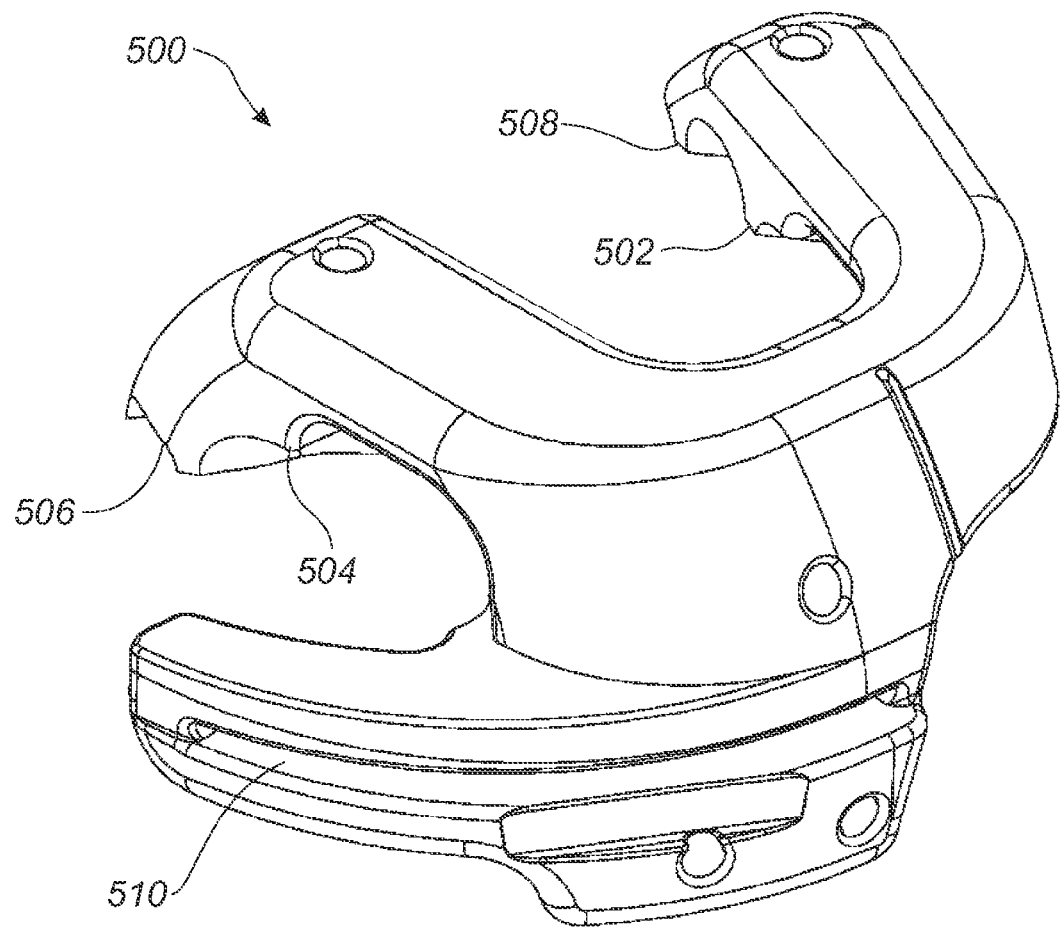
FIG. 5 illustrates a patient matched cutting guide, in this particular embodiment, a cutting guide for guiding a resection of a proximal tibia.
Figure 6:
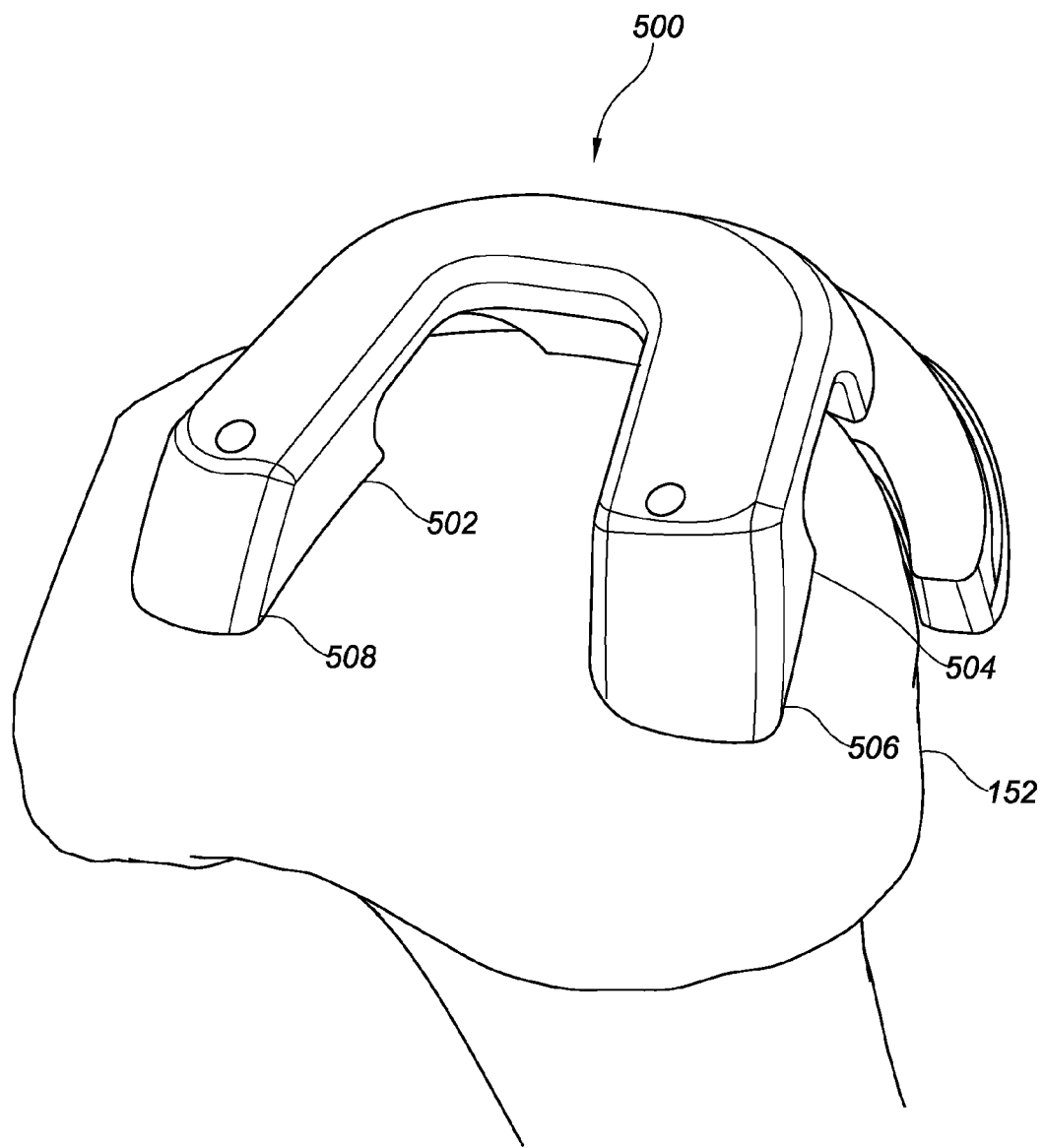
FIG. 6 illustrates a patient matched cutting guide in place on a patient's bone.

Once an ideal positioning and orientation of the selected implant component is determined, the embodiment of method 200 proceeds to block 214 wherein custom bone preparation information is provided to a surgeon or other user. In the embodiment illustrated in FIG. 2, a patient-matched cutting guide is created to facilitate preparation of bony surfaces of joint 150. According to other embodiments, providing custom bone preparation information may include providing measurements or other guidance to a surgeon or other user for making ideal bone preparation. In the example shown in FIG. 2, a patient-matched cutting guide may be rapidly created using a number of techniques. For example, rapid manufacturing equipment can be used to create a cutting guide configured to match the unique surface anatomy of the patient's joint surface. As illustrated in FIG. 5, a custom guide 500 includes surface contact points 502-508. Note that custom guide 500 includes many surface contact points, but for illustration purposes only a handful are numbered in FIG. 5. The surface contact points 502-508 are designed based on the surface information derived from the scan of joint surface 150 such that they are the precise height and shape to match the outer surface of the bone and/or cartilage being prepared with the cutting block. For example, the cutting guide 500 can be placed against a tibia 152 as shown in FIG. 6. Contact points 502-506 can be seen to rest firmly on the tibial surface, despite the unique geometry of the tibia 152, because they have been custom made to match that unique geometry. The contact surfaces can form a single contiguous contact surface that is a mirror image of the joint surface or may be configured to only contact the joint surface in certain predetermined locations.

In some embodiments, an adjustable cutting device can be made to match the surface anatomy of the patient by adjusting set screws or other adjustable structures so that they contact determined points on the joint surface. The adjustment of the set screws can be facilitated by the processing unit 104, which can provide to the user a set of measurement specifying an adjustment amount for each variable portion of the adjustable cutting device in order to cause each adjustable portion to precisely align with, and contact, the particular joint surface of the patient.

According to certain embodiments, a CAS system may be used in place of a cutting block to guide bone preparation so that the implant is positioned and spatially oriented to the optimal position. Using a CAS system may cut down on time to create or configure a cutting block for a particular patient. Using a CAS system may also be advantageous in that it may be used in conjunction with the simulation software to compare a predicted (pre-surgical) performance result with an actual (post-surgical) performance result. In this way, once actual cuts are made, the CAS system can compare the actual cut location with the suggested cut location and output a determination of actual performance loss or gain from the originally suggested surgical plan.

The embodiment of the patient-matched guide shown in FIGS. 5 and 6 facilitates preparation of the anatomy of the joint 150. For example, custom guide 500 includes a slot 510 that guides a resection of tibia 152 once contact points 502-508 are situated against the tibia 152. The exact orientation of the slot 510 can be adjusted relative to the contact points 502-508 in order to achieve a resection that will yield ideal implant location and orientation. Because the modeling processor 108 has a virtual three-dimensional model of the joint and prosthetic components that incorporates information regarding the mechanical axes of the joint, bone morphology, and ligament attachment points, it can identify the exact resection location on the bone relative to the joint surface that will yield preferred implant placement. The location of the resection relative to the joint surfaces can be translated to the relative position of the slot 510 relative to contact points 502-508 by the modeling processor 108 and incorporated into a rapid prototype cutting block, translated to adjustment amounts for variable portions of an adjustable cutting guide, or otherwise converted into measurements that can be communicated to a surgeon for use with CAS or with conventional, non-guided surgical equipment used to make the bone preparation.

Once a patient-matched guide is created, the embodiment of method 200 proceeds to block 216 wherein the joint surface is prepared using the patient-matched guide, and the implant components are placed in the optimal position and orientation based on the joint surface preparations. According to certain embodiments, after the implant components are placed, a second intra-operative optical scan may be obtained. Data from the second optical scan may then be compared with the computer model and predicted implant location to determine how accurately the implant component placement was achieved and identify any needed corrections from the actual location and the predicted ideal placement. Once the implant components are placed and the surgeon is satisfied with the results, the surgical procedure may be concluded according to sound medical technique.

Various embodiments of the invention have been described in fulfillment of the various objectives of the invention. It should be recognized that these embodiments are merely illustrative of the principles of the present invention. Numerous modifications and adaptations thereof will be readily apparent to those of skill in the art without departing from the spirit and scope of the invention.

The invention claimed is:

1. A method for implanting an implant relative to a joint, comprising:
(a) exposing through one or more incisions a joint of a patient;

(b) marking ligament attachment points associated with the joint with markers prior to scanning the exposed joint;
(c) scanning the exposed joint using an optical scanner to obtain image data, including position of the markers, wherein
the image data is used by a computer processor to create a computer model of the joint and to identify
at least one optimal implant attribute; and
(d) implanting an implant relative to the joint, wherein the implant includes the identified optimal implant attribute.

2. The method of claim 1, wherein exposing the joint comprises exposing a knee joint.

3. The method of claim 2, wherein exposing the knee joint comprises exposing articular surfaces and ligament attachment points associated with the knee joint.

4. The method of claim 1, wherein scanning the exposed joint using the optical scanner comprises scanning the exposed joint using a topographical scanner.

5. The method of claim 1, wherein scanning the exposed joint comprises scanning surfaces associated with a tibia, a femur, and a patella.

6. The method of claim 1, wherein creating the computer model of the joint comprises creating a three-dimensional computer model of the joint.

7. The method of claim 1, wherein creating the computer model of the joint comprises creating a computer model of the joint incorporating information relating a mechanical axis to the joint.

8. The method of claim 1, wherein creating the computer model of the joint comprises creating a computer model of the joint incorporating information relating at least one ligament attachment location to the joint.

9. The method of claim 1, wherein identifying at least one optimal implant attribute comprises using the computer processor and the computer model of the joint to simulate the implant implanted relative to the joint.

10. The method of claim 9, wherein simulating the implant implanted relative to the joint comprises simulating movement of the joint after implantation of the implant.

11. The method of claim 10, wherein simulating the implant implanted relative to the joint comprises simulating a potential implant component for implantation relative to the joint.

12. The method of claim 11, wherein simulating the potential implant component comprises simulating a possible implant component selected from a library of possible implant components.

13. The method of claim 10, wherein simulating the implant implanted relative to the joint comprises simulating a potential implant position and orientation for implantation relative to the joint.

14. The method of claim 1, further comprising using the computer model of the joint and the identified optimal implant attribute to determine custom bone preparation information.

15. The method of claim 14, further comprising using the custom bone preparation information to rapidly manufacture a custom cutting guide.

16. The method of claim 14, further comprising using the custom bone preparation information to adjust an adjustable cutting device.

17. A method of identifying at least one optimal implant attribute relative to a joint of a patient, comprising:
(a) exposing through one or more incisions a joint of a patient;
(b) marking ligament attachment points associated with the joint with markers prior to scanning the exposed joint; and
(c) scanning the exposed joint using an optical scanner to obtain image data, including position of the markers, wherein the image data is used by a computer processor to create a computer model of the joint and to identify at least one optimal implant attribute.

* * * * *